United States Patent [19]

Drabek

[11] Patent Number: 5,068,441
[45] Date of Patent: Nov. 26, 1991

[54] N-BENZOYL-N'TRIHALO-HALOALKOXY-PHENYLUREAS AND PESTICIDAL COMPOSITIONS CONTAINING THEM

[75] Inventor: Josef Drabek, Oberwil, Switzerland

[73] Assignee: Ciba-Geigy Corporation, Ardsley, N.Y.

[21] Appl. No.: 485,119

[22] Filed: Feb. 23, 1990

Related U.S. Application Data

[62] Division of Ser. No. 187,173, Apr. 28, 1988, Pat. No. 4,925,876.

[30] Foreign Application Priority Data

May 8, 1987 [CH] Switzerland .......................... 1753/87

[51] Int. Cl.$^5$ .................. C07C 211/52; C07C 275/54; A01N 47/34
[52] U.S. Cl. ...................................... 564/442; 564/44
[58] Field of Search ................... 564/442, 44; 514/594

[56] References Cited

U.S. PATENT DOCUMENTS 4,457,943 7/1984 Becher et al. ..................... 514/594
4,711,905 12/1987 Sirrenberg et al. ............... 514/594

FOREIGN PATENT DOCUMENTS 0071279 2/1983 European Pat. Off. .
0194688 9/1986 European Pat. Off. .
0237056 10/1985 Japan .
0872742 4/1987 South Africa .

Primary Examiner—Richard L. Raymond
Assistant Examiner—Peter G. O'Sullivan
Attorney, Agent, or Firm—Edward McC. Roberts

[57] ABSTRACT

The invention relates to novel substituted N-benzoyl-N'-2,3,5-trihalo-4-haloalkoxyphenylureas of formula I

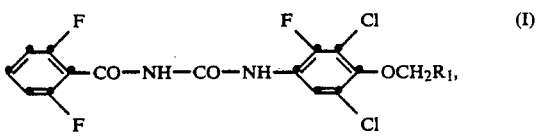

wherein $R_1$ is $CF_3$, $CF_2CF_3$ or $CF_2F_2CF_3$, to the preparation of these compounds and to intermediates for their synthesis. The invention further relates to the use of the novel compounds for use in pest control and to pesticidal compositions which contain at least one compound of formula I as active component. The preferred utility is the control of pests of animals and plants.

4 Claims, No Drawings

N-BENZOYL-N'TRIHALO-HALOALKOXY-PHENYLUREAS AND PESTICIDAL COMPOSITIONS CONTAINING THEM

This is a divisional of application Ser. No. 187,173 filed on Apr. 28, 1988, now U.S. Pat. No. 4,925,876.

The present invention relates to novel substituted N-benzoyl-N'-2,3,5-trihalo-4-haloalkoxyphenylureas, to a process for their preparation and to intermediates for their synthesis, to pesticidal compositions which contain these novel compounds and to the use thereof in pest control.

The novel compounds have the formula I

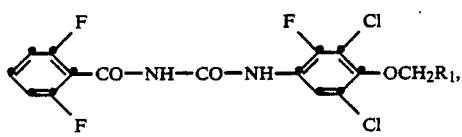

wherein $R_1$ is $CF_3$, $CF_2CF_3$ or $CF_2CF_2CF_3$.

Among the compounds of formula I, the preferred compound is that in which $R_1$ is $CF_2CF_3$.

The compounds of this invention can be prepared by methods which are known per se. Such methods are disclosed, for example, in German Offenlegungsschrift specifications 2 123 236, 2 601 780 and 3 240 975. Thus, for example, the compounds of formula I can be obtained by a) reacting an aniline of formula II

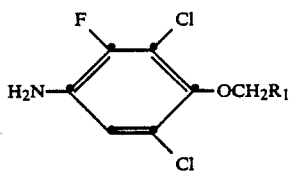

with the benzoyl isocyanate of formula III

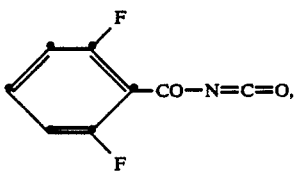

or b) reacting an isocyanate of formula IV

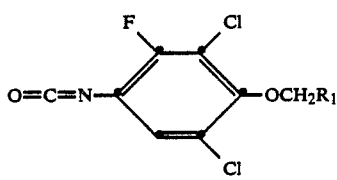

with the benzamide of formula V

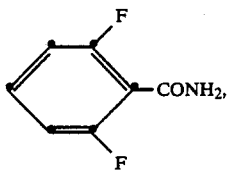

or c) reacting an aniline of formula II with a urethane of formula VI

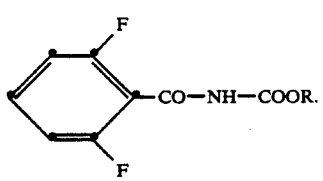

In formulae II and IV above $R_1$ is as defined for formula I and, in formula VI, R is a $C_1$-$C_8$alkyl radical which is unsubstituted or is substituted by halogen, preferably chlorine.

The above processes a), b) and c) can preferably be carried out under normal pressure and in the presence of an organic solvent or diluent. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons, preferably benzene, toluene, xylene, chloroform, methylene chloride, carbon tetrachloride and chlorobenzene; nitriles such as acetonitrile or propionitrile; dimethyl sulfoxide; and ketones, e.g. acetone, methyl ethyl ketone, methyl isopropyl ketone and methyl isobutyl ketone. Process a) is normally carried out in the temperature range from $-10°$ to $+200°$ C., preferably from 0° to 150° C., if desired in the presence of an organic base, e.g. triethylamine. Process b) is carried out in the temperature range from 0° to 150° C., preferably at the boiling point of the solvent employed and, if desired, in the presence of an organic base such as pyridine, and/or with the addition of an alkali metal or alkaline earth metal, preferably sodium. For the reaction of the urethane of formula VI with an aniline of formula II according to process c), a temperature range from about 60° C. to the boiling point of the reaction mixture is preferred, and the solvent employed is preferably an aromatic hydrocarbon such as toluene, xylene, chlorobenzene and the like.

The starting materials of formulae III to VI are known or can be prepared by methods analogous to known ones.

The starting materials of formula II are novel compounds, which also constitute an object of the present invention. The compounds of formula II can be prepared in a manner known per se, for example by hydrogenating a suitably substituted nitrobenzene of formula VII

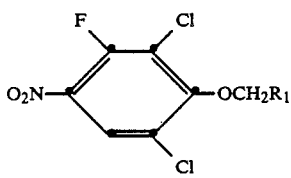

in a manner analogous to that described in J. Org. Chem. 29 (1964), 1, (q.v. also the literature cited in this reference). However, anilines of formula II can also be obtained by chemical reduction (e.g. with Sn(II) chloride/HCl) of the corresponding nitro compounds of formula VII (q.v. Houben-Weyl, Methoden d. org. Chemie, 11/1, 422). A further means of preparing anilines of formula II comprises appropriately haloalkylating free or acylated 2-fluoro-3,5-dichloro-4-hydroxyaniline and then removing the acyl group, if present, for example by acid hydrolysis.

The nitro compounds of formula VII are likewise novel and constitute an object of the present invention. They can be obtained, for example, by appropriate haloalkylation of 2-fluoro-3,5-dichloro-4-nitrophenol (q.v. French patent specification 2 005 876) or by reaction of 2,4-difluoro-3,5-dichloronitrobenzene with a suitable polyfluoroalkanol in alkaline solution and dimethyl sulfoxide as solvent (q.v. "The Chemistry of the Hydroxyl Group", pp. 83–124, Interscience Publishers Inc., New York, 1971).

The benzoylisocyanate of formula III can be obtained, for example, as follows (q.v. J. Agr. Food Chem. 21, 348 and 993; 1973):

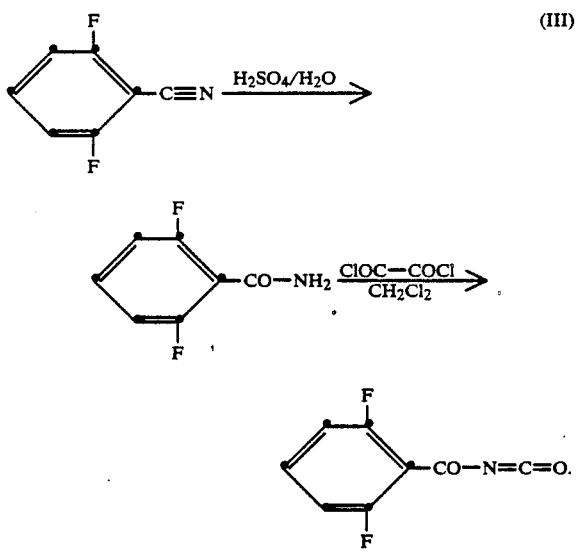

The 4-(polyfluoroalkoxy)phenylisocyanates of formula IV can be prepared, for example, by phosgenating an aniline of formula II by methods which are commonly known in the art. The benzamide of formula V also employed as starting material is known (q.v. for example Beilstein, "Handbuch der organischen Chemie", Vol. 9, p. 336).

The urethane of formula VI can be obtained in a manner known per se by reacting the benzoylisocyanate of formula III with a suitable alcohol or by reacting the benzamide of formula V, in the presence of a base, with a corresponding ester of chloroformic acid Cl—COOR.

Published European patent application 0 071 279 broadly discloses, for example, N-halobenzoyl-N'-(halo-4-haloalkoxy)phenylureas as insecticides with larvacidal activity. Published European patent application 0 194 688 also broadly discloses N-dihalobenzoyl-N'-(halo-4-fluoroalkoxy)phenylureas as insecticides with ovicidal and larvicidal activity. In neither of these two publications, however, are N-(2,6-difluorobenzoyl)-N'-(2-fluoro-3,5-dichloro-4-trifluoroethoxy, -pentafluoropropoxy or -heptafluorobutoxy)phenylureas specifically disclosed.

Surprisingly, it has been found that the compounds of formula I of this invention are more effective pesticides while being well tolerated by warm-blooded animals and plants. The compounds of formula I are therefore suitable e.g. for controlling pests of animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, e.g. in fruit and vegetable crops, and especially in cotton crops. If compounds of formula I are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the chief pests are ectoparasites, such as mites and ticks and Diptera, for example *Lucilia sericata*.

In particular the compounds of this invention are distinguished by their excellent larvicidal action against *Spodoptera littoralis* and *Heliothis virescens*.

The good pesticidal activity of the compounds of formula I corresponds to a mortality of at least 50–60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLE 1: PREPARATION

1.1. Intermediates

1.1.1. Nitrobenzenes 1.1.1.1. 2-Fluoro-3,5-dichloro-4-(2',2',3',3',3'-pentafluoropropoxy)nitrobenzene 12.4 g of 90% potassium hydroxide are suspended in 80 ml of dimethyl sulfoxide. With stirring, 30 g of 2',2',3',3',3'-pentafluoropropanol are added dropwise to this suspension. The resultant solution is then added dropwise at room temperature, with stirring, to a solution of 52.4 g of 2,4-difluoro-3,5-dichloronitrobenzene in 150 ml of dimethyl sulfoxide. When the dropwise addition is complete, the reaction mixture is stirred for 2 hours at room temperature and then concentrated. The crude product is dissolved in methylene chloride and the methylene chloride solution is washed with water and dried and, finally, the solvent is distilled off. The crude product is purified by chromatography through a column of silica gel using a 19:1 mixture of hexane/ether as eluant. The solvent is then distilled off, affording yellow crystals of the title compound of formula

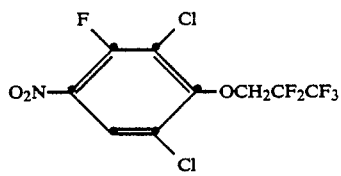

(compound 1.1.1.1.)

with a melting point of 62°–63° C.

The following compounds are prepared in analogous manner:

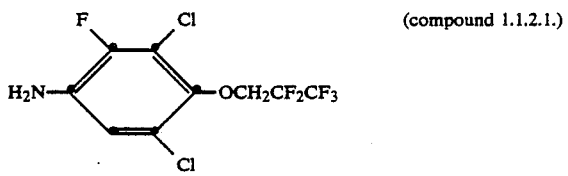

| Compound | R₁ | m.p. °C. |
|---|---|---|
| 1.1.1.2. | CF₃ | 50–51 |
| 1.1.1.3. | CF₂CF₂CF₃ | 54–55 |

1.1.2. Anilines 1.1.2.1. 2-Fluoro-3,5-dichloro-4-(2',2',3',3',3'-pentafluoropropoxy)aniline 6.2 g of the above nitrobenzene are dissolved in 60 ml of tetrahydrofuran and the solution is hydrogenated at room temperature for 8 hours in the presence of 2 g of Raney nickel (H₂ absorption: 1.2 l). The reaction mixture is filtered, the solvent is distilled off, and the residue distilled. The title compound of formula

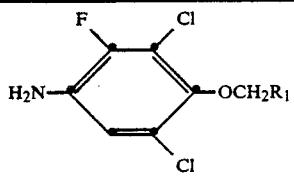

(compound 1.1.2.1.)

has a boiling point of 170° C./0.06 torr.

The following compounds are prepared in analogous manner:

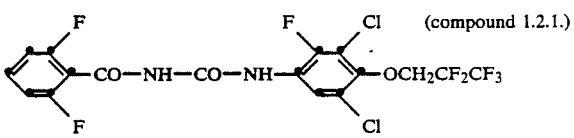

| Compound | R₁ | Physical data |
|---|---|---|
| 1.1.2.2. | CF₃ | m.p. 32–35° C. |

| Compound | R₁ | Physical data |
|---|---|---|
| 1.1.2.3. | CF₂CF₂CF₃ | b.p. 140° C./0.03 torr |

1.2. Final products 1.2.1. N-(2,6-Difluorobenzoyl)-N'-[2-fluoro-3,5-dichloro-4-(2',2',3',3',3'-pentafluoropropoxy)phenyl]urea A solution of 3.3 g of 2,6-difluorobenzoylisocyanate in 10 ml of dry toluene is added to a solution of 2-fluoro-3,5-dichloro-4-(2',2',3',3',3'-pentafluoropropoxy)aniline in 50 ml dry toluene, and the mixture is stirred for 10 hours. Then about 75% of the solvent is removed in a rotary evaporator. The precipitate is filtered with suction, washed with a small amount of cold toluene and hexane and dried under vacuum, affording the title compound of formula (compound 1.2.1.)

in the form of a white crystalline powder with a melting point of 176°–179° C.

The following compounds are prepared in analogous manner:

| Compound | R₁ | m.p. °C. |
|---|---|---|
| 1.2.2. | CF₃ | 192–193 |
| 1.2.3. | CF₂CF₂CF₃ | 163–164 |

EXAMPLE 2

Formulations of compounds of formula I according to Preparatory Example 1.2. (Throughout, Percentages are by Weight)

| 2.1. Emulsifiable concentrate | |
|---|---|
| a compound according to Preparatory Example 1.2. | 10% |
| castor oil polyethylene glycol ether (36 mol of ethylene oxide) | 25% |
| butanol | 15% |
| ethyl acetate | 50% |

Emulsions of any required concentration can be produced from such concentrates by dilution with water.

| 2.2. Solutions | a) | b) |
|---|---|---|
| a compound according to Preparatory Example 1.2. | 10% | 5% |
| polyethylene glycol 400 | 70% | — |
| N-methyl-2-pyrrolidone | 20% | 20% |
| epoxidised coconut oil | — | 1% |
| petroleum distillate (boiling range 160-190° C.) | — | 74% |

These solutions are suitable for application in the form of microdrops.

| 2.3. Granulates | a) | b) |
|---|---|---|
| a compound according to Preparatory Example 1.2. | 5% | 10% |
| kaolin | 94% | — |
| highly dispersed silicic acid | 1% | — |
| attapulgite | — | 90% |

The active ingredient or ingredients is or are dissolved in methylene chloride, the solution is sprayed onto the carrier, and the solvent is subsequently evaporated off in vacuo.

| 2.4. Extruder granulate | |
|---|---|
| a compound according to Preparatory Example 1.2. | 10% |
| sodium lignosulfonate | 2% |
| carboxymethylcellulose | 1% |
| kaolin | 87% |

The active ingredient or ingredients is or are mixed and ground with the adjuvants, and the mixture is subsequently moistened with water. The mixture is extruded and then dried in a stream of air.

| 2.5. Coated granulate | |
|---|---|
| a compound according to Preparatory Example 1.2. | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | a) | b) | c) | d) |
|---|---|---|---|---|
| a compound according to Preparatory Example 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and, optionally, grinding the mixture in a suitable mill.

| 2.7. Wettable powders | a) | b) | c) |
|---|---|---|---|
| a compound according to Preparatory Example 1.2. | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether | — | 2% | — |

-continued

| 2.7. Wettable powders | a) | b) | c) |
|---|---|---|---|
| (7-8 mol of ethylene oxide) | | | |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound according to Preparatory Example 1.2. | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological Tests 3.1. Action against *Musca domestica*

50 g of freshly prepared nutrient substrate for maggots are weighed into a beaker. Then 5 ml of a 1% acetonic solution of the test compound are pipetted onto the nutrient substrate present in the beaker. The substrate is then thoroughly mixed and the acetone subsequently allowed to evaporate over a period of at least 20 hours.

Then 25 one-day-old maggots of *Musca domestica* are put into the beaker containing the treated nutrient substrate. After the maggots have pupated, the pupae are separated from the substrate by flushing them out with water and then deposited in a container closed with a perforated top.

The flushed out pupae are counted to determine the toxic effect of the test compound on the maggot development. A count is then made after 10 days of the number of flies which have hatched out of the pupae.

The compounds of Example 1.2. exhibit good activity in this test.

3.2. Action against *Lucilia sericata*

1 ml of an aqueous solution containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate.

In this test, compounds of Example 1.2. exhibit good activity against *Lucilia sericata*.

3.3. Action against *Aedes aegypti*

A specific amount of a 0.1% solution of the test compound in acetone is pipetted onto the surface of 150 ml of water in a beaker to give a concentration of 12.5 ppm.

After the acetone has evaporated, 30 to 40 two-day-old larvae of Aedes aegypti are put into the beaker containing the test compound. Mortality counts are made after 2 and 7 days.

In this test, compounds of Example 1.2. exhibit good activity against Aedes aegypti.

3.4. Stomach toxicant action against Spodoptera littoralis and Heliothis virescens larvae ($L_1$)

Cotton plants in the cotyledon stage are sprayed with an aqueous emulsion (obtained from a 10% emulsifiable concentrate) containing 3, 1.5, 0.8, 0.4 and 0.2 ppm of the test compound. After the spray coating has dried, each cotton plant is populated with Spodoptera littoralis and Heliothis virescens larvae in the $L_1$-stage. The test is carried out at 26° C. and ca. 50% relative humidity. After 6 days a mortality count is made of the larvae present on the plants.

ation is made to determine the percentage mortality of the larvae.

Compounds of Example 1.2. effect 80–100% kill after 2 and 5 days.

3.7. Action against Laspeyresia pomonella (eggs)

Egg deposits of Laspeyresia pomonella not more than 24 hours old are immersed on filter paper for 1 minute in an aqueous acetonic solution containing 400 ppm of the test compound.

After the solution has dried, the eggs are placed in petri dishes and kept at a temperature of 28° C. The percentage of larvae hatched from the treated eggs is evaluated after 6 days.

The compounds of Example 1.2. exhibit good activity in this test.

3.8. Influence on the reproduction of Anthonomous

| | | Percentage mortality after 6 days and at a concentration of | | | | |
|---|---|---|---|---|---|---|
| | | | 3 ppm | 1.5 ppm | 0.8 ppm | 0.4 ppm | 0.2 ppm |
| A | Compound 1.2.1 (structure with $CO-NH-CO-NH$ linking two fluorinated phenyl rings, $OCH_2CF_2CF_3$) | Spodoptera littoralis $L_1$ | 100 | 100 | 100 | 100 | 80 |
| | | Heliothis virescens $L_1$ | 100 | 100 | 90 | 53 | 0 |
| B | European patent application 0 071 279 Compound 48 (structure with $CO-NH-CO-NH$ linking two fluorinated phenyl rings, $OCF_2CHF_2$) | Spodoptera littoralis $L_1$ | 100 | 97 | 70 | 0 | 0 |
| | | Heliothis virescens $L_1$ | 100 | 67 | 7 | 0 | 0 |

Compound 1.2.1. of Example 1.2. has a significantly greater activity at the same concentration.

3.5. Stomach toxicant action against Spodoptera littoralis and Heliothis vireschens larvae ($L_3$)

Potted soybean plants (pot size: 10 cm diameter) in the 4-leaf stage are sprayed with aqueous emulsions which contain the test compound in a concentration of 0.75 ppm.

After 2 days, each treated soybean plant is populated with 10 larvae of Spodoptera littoralis and Heliothis virescens in the $L_3$-stage. The test is carried out at 26° C. and ca. 60% relative humidity in dim light. After 2 and 5 days evaluation is made to determine the percentage mortality of the larvae.

Compounds of Example 1.2. effect 80–100% kill against Spodoptera and Heliothis after 2 and 5 days.

3.6. Insecticidal stomach toxicant action against Plutella xylostella larvae ($L_2$)

Potted Chinese cabbage plants (pot size: 10 cm diameter) in the 4-leaf stage are sprayed with aqueous emulsions which contain the test compound in a concentration of 0.75 ppm.

After 2 days, each treated Chinese cabbage plant is populated with 10 Plutella xylostella larvae in the $L_2$-stage. The test is carried out at 26° C. and ca. 60% relative humidity in dim light. After 2 and 5 days evalugrandis Anthonomous grandis adults which are not more than 24 hours old after hatching are transferred in groups of 25 to barred cages. The cages are then immersed for 5 to 10 seconds in an acetonic solution containing 0.1% by weight of the test compound. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

The compounds of Example 1.2. exhibit a good reproduction inhibiting effect in this test.

3.9. Action against Anthonomus grandis (adults)

Two cotton plants in the 6-leaf stage, in pots, are each sprayed with a wettable aqueous emulsion formulation containing 100 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of Example 1.2. exhibit good activity in this test.

3.10. Action against *Epilachna varivestis*

Phaseolus vulgaris plants (dwarf beans) about 15–20 cm in height are sprayed with aqueous emulsion formulations of the test compound in concentrations of 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

Compounds of Example 1.2. exhibit good activity in this test.

3.11. Ovicidal action against *Heliothis virescens* and *Spodoptera littoralis*

Appropriate amounts of a wettable powder formulation containing 25% by weight of the test compound are mixed with sufficient water to produce an aqueous emulsion with an active ingredient concentration of 400 ppm. One-day-old egg deposits of Heliothis on cellophane and egg deposits of Spodoptera on paper are immersed in these emulsions for 3 minutes and then collected by suction on round filters. The treated deposits are placed in petri dishes and kept in the dark at 28° C. and 60% relative humidity. The hatching rate, i.e. the number of larvae that have hatched from the treated eggs, in comparison with untreated controls is determined after 5 to 8 days.

Compounds of Example 1.2. effect 80-100% ovicidal action (kill) in this test against *Heliothis virescens* and *Spodoptera littoralis*.

What is claimed is:

1. A compound of formula II

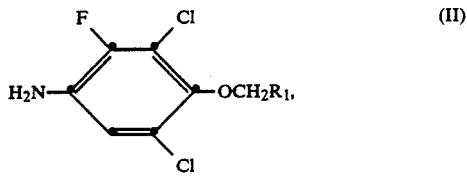

wherein $R_1$ is $CF_3$, $CF_2CF_3$ or $CF_2CF_2CF_3$.

2. A compound according to claim 1 of formula

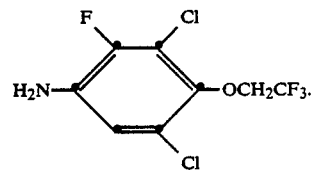

3. A compound according to claim 1 of formula

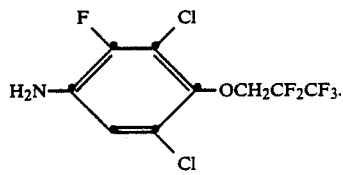

4. A compound according to claim 1 of formula

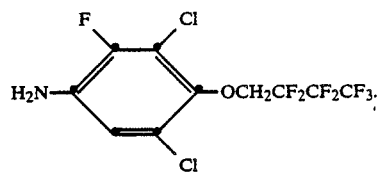

* * * * *